(12) United States Patent
Sonoda et al.

(10) Patent No.: US 12,745,339 B2
(45) Date of Patent: Sep. 22, 2026

(54) X-RAY TUBE DEVICE AND X-RAY CT APPARATUS

(71) Applicant: FUJIFILM Healthcare Corporation, Chiba (JP)

(72) Inventors: Ren Sonoda, Kashiwa (JP); Yutaro Tanabe, Kashiwa (JP); Kimihiro Nakayama, Kashiwa (JP)

(73) Assignee: FUJIFILM Healthcare Corporation, Chiba (JP)

( * ) Notice: Subject to any disclaimer, the term of this patent is extended or adjusted under 35 U.S.C. 154(b) by 181 days.

(21) Appl. No.: 18/629,874

(22) Filed: Apr. 8, 2024

(65) Prior Publication Data

US 2024/0347309 A1 Oct. 17, 2024

(30) Foreign Application Priority Data

Apr. 14, 2023 (JP) ................................ 2023-066336

(51) Int. Cl.

| | |
|---|---|
| ***A61B 6/03*** | (2006.01) |
| ***A61B 6/00*** | (2006.01) |
| ***H01J 35/16*** | (2006.01) |
| ***H01J 35/26*** | (2006.01) |
| ***H05G 1/02*** | (2006.01) |

(52) U.S. Cl.

CPC ............ *H05G 1/025* (2013.01); *A61B 6/035* (2013.01); *A61B 6/4488* (2013.01); *H01J 35/16* (2013.01);

(Continued)

(58) Field of Classification Search

None

See application file for complete search history.

(56) References Cited

U.S. PATENT DOCUMENTS 4,768,212 A * 8/1988 Appelt .................. H05G 1/025 313/36
6,430,263 B1 * 8/2002 Lu ......................... H05G 1/025 378/127

(Continued)

FOREIGN PATENT DOCUMENTS

EP 1840934 A1 * 10/2007 ............. H01J 35/26
EP 1338025 6/2009

(Continued)

OTHER PUBLICATIONS

"Search Report of Europe Counterpart Application", issued on Sep. 4, 2024, pp. 1-5.

(Continued)

*Primary Examiner* — Thomas R Artman
(74) *Attorney, Agent, or Firm* — JCIPRNET

(57) ABSTRACT

Provided are an X-ray tube device and an X-ray CT apparatus, which are capable of improving cooling efficiency of a stator coil together with cooling efficiency of an X-ray window.

An X-ray tube device includes an X-ray tube including an envelope that holds, in a vacuum, a cathode generating an electron beam and an anode emitting an X-ray by collision of the electron beam, and an X-ray window through which the X-ray is transmitted; a stator coil configured to generate a driving force for rotating the anode; a tube container configured to accommodate the X-ray tube and the stator coil together with insulating oil; and a cooler configured to cool the insulating oil, in which the X-ray tube device further includes a first inflow port connected to a pipe linking the tube container and the cooler and disposed near the X-ray window, a second inflow port connected to the pipe and disposed near the stator coil, and a controller configured to cause the insulating oil to flow into the tube container through the first inflow port in a case where the (Continued)

X-ray is emitted and to cause the insulating oil to flow into the tube container through the second inflow port in a case where the X-ray is not emitted.

7 Claims, 8 Drawing Sheets

(52) U.S. Cl.
CPC ....... *H01J 35/26* (2013.01); *H01J 2235/1026* (2013.01); *H01J 2235/1216* (2013.01); *H01J 2235/122* (2013.01); *H01J 2235/127* (2013.01)

(56) References Cited

U.S. PATENT DOCUMENTS

| | | | | |
|---|---|---|---|---|
| 6,511,224 | B1 * | 1/2003 | Lu | H05G 1/025 378/141 |
| 2007/0230662 | A1 * | 10/2007 | Imai | H05G 1/025 378/130 |
| 2024/0347309 | A1 * | 10/2024 | Sonoda | A61B 6/4488 |

FOREIGN PATENT DOCUMENTS

| | | | | |
|---|---|---|---|---|
| EP | 1707036 | | 12/2010 | |
| JP | S58216346 A | * | 12/1983 | H01J 35/10 |
| JP | 2004152680 | | 5/2004 | |

OTHER PUBLICATIONS

"Office Action of Europe Counterpart Application", issued on Jul. 17, 2025, pp. 1-4.

* cited by examiner

X-RAY TUBE DEVICE AND X-RAY CT APPARATUS

CLAIM OF PRIORITY

The present application claims priority from Japanese Patent Application JP 2023-066336 filed on Apr. 14, 2023, the content of which is hereby incorporated by reference into this application.

BACKGROUND OF THE INVENTION

1. Field of the Invention

The present invention relates to an X-ray tube device and an X-ray computed tomography (CT) apparatus, and particularly relates to cooling of the X-ray tube device.

2. Description of the Related Art

An X-ray CT apparatus generates a tomographic image of a subject using projection data that is obtained from multiple directions by rotating an X-ray tube device, which irradiates the subject with X-rays, and an X-ray detector, which detects the X-rays transmitted through the subject, around the subject. The generated tomographic image depicts a shape of an organ within the subject and is used for image diagnosis.

An X-ray tube device includes an X-ray tube that holds a cathode and an anode in a vacuum; and a tube container that accommodates the X-ray tube together with insulating oil, and emits an X-ray from an X-ray focus by causing an electron beam that is released from the cathode and accelerated by a high voltage applied between the cathode and the anode to collide with the X-ray focus on the anode. Since about 99% of the energy of the electron beam colliding with the anode is converted into heat, cooling of the X-ray tube device, particularly cooling of an X-ray window which is provided near the X-ray focus and through which X-rays is transmitted is important.

JP2004-152680A discloses an X-ray tube device configured to flow insulating oil cooled by a cooler toward an X-ray window and to flow a part of the insulating oil in a direction opposite to a direction toward the X-ray window. With such a configuration, the X-ray window that is locally heated is cooled, and sedimentation of the insulating oil flowing in the X-ray tube device is suppressed.

SUMMARY OF THE INVENTION

However, in JP2004-152680A, consideration for cooling a stator coil that generates a rotational driving force of an anode of an X-ray tube device is insufficient. In the X-ray tube device, an increase in heat capacity of the anode is required, and the anode is increased in weight in accordance with the increase in heat capacity. With the increase in the weight of the anode, it is necessary to increase the rotational driving force of the anode, and thus heat generated by the stator coil is increased.

Therefore, an object of the present invention is to provide an X-ray tube device and an X-ray CT apparatus including the X-ray tube device, which are capable of improving cooling efficiency of a stator coil together with cooling efficiency of an X-ray window.

In order to achieve the above object, an X-ray tube device according to an aspect of the present invention comprises an X-ray tube including an envelope that holds, in a vacuum, a cathode generating an electron beam and an anode emitting an X-ray by collision of the electron beam, and an X-ray window through which the X-ray is transmitted; a stator coil configured to generate a driving force for rotating the anode; a tube container configured to accommodate the X-ray tube and the stator coil together with insulating oil; and a cooler configured to cool the insulating oil, in which the X-ray tube device includes a first inflow port connected to a pipe linking the tube container and the cooler and disposed near the X-ray window, a second inflow port connected to the pipe and disposed near the stator coil, and a controller configured to cause the insulating oil to flow into the tube container through the first inflow port in a case where the X-ray is emitted and to cause the insulating oil to flow into the tube container through the second inflow port in a case where the X-ray is not emitted.

In addition, an X-ray CT apparatus according to an aspect of the present invention is an X-ray CT apparatus that generates a tomographic image of a subject, the X-ray CT apparatus comprises the X-ray tube device.

According to the present invention, it is possible to provide the X-ray tube device and the X-ray CT apparatus including the X-ray tube device, which are capable of improving the cooling efficiency of the stator coil together with the cooling efficiency of the X-ray window.

DESCRIPTION OF THE PREFERRED EMBODIMENTS

Figure 1:
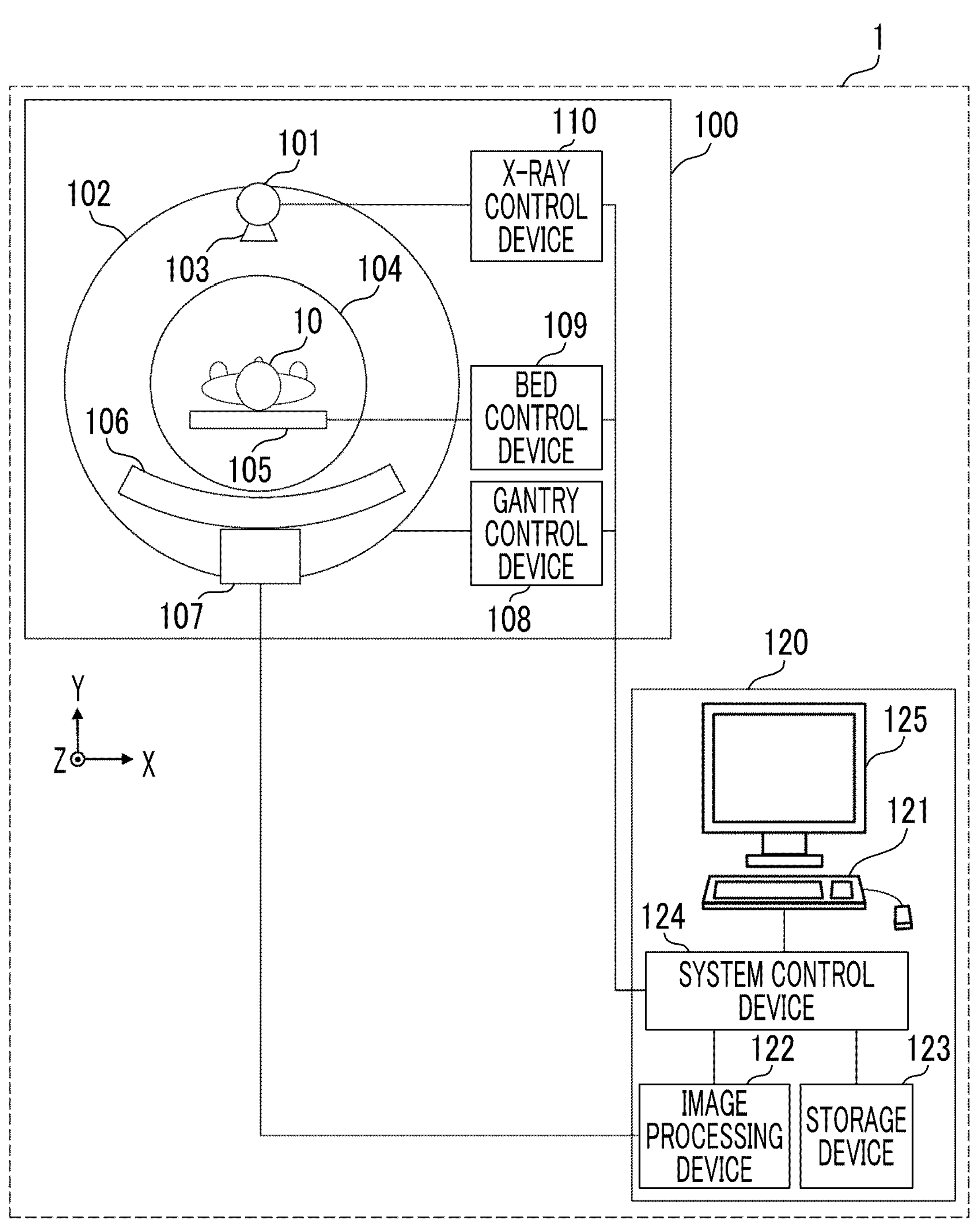
FIG. 1 is a diagram showing an overall configuration of an X-ray CT apparatus.

Hereinafter, a preferred embodiment of an X-ray tube device and an X-ray CT apparatus according to an aspect of the present invention will be described with reference to the accompanying drawings. In the following description and the accompanying drawings, components having the same functional configuration are designated by the same reference numerals, and thereby duplicate description thereof will not be repeated.

An example of an overall configuration of an X-ray CT apparatus 1 will be described with reference to FIG. 1. The X-ray CT apparatus 1 comprises a scan gantry unit 100 and an operation unit 120.

The scan gantry unit 100 comprises an X-ray tube device 101, a rotary disc 102, a collimator 103, an X-ray detector 106, a data collection device 107, a bed device 105, a gantry control device 108, a bed control device 109, and an X-ray control device 110. The X-ray tube device 101 is a device that irradiates a subject 10 placed on the bed device 105 with X-rays. The collimator 103 is a device that restricts an irradiation range of X-rays. The rotary disc 102 comprises an opening portion 104 into which the subject 10 placed on the bed device 105 enters, is provided with the X-ray tube device 101 and the X-ray detector 106, and rotates the X-ray tube device 101 and the X-ray detector 106 around the subject 10.

The X-ray detector 106 is a device that is disposed to face the X-ray tube device 101 and that measures a spatial distribution of transmitted X-rays by detecting X-rays transmitted through the subject 10. Detection elements of the X-ray detector 106 are arranged two-dimensionally in a rotation direction and a rotation axis direction of the rotary disc 102. The data collection device 107 is a device that collects an X-ray dose detected by the X-ray detector 106 as digital data. The gantry control device 108 is a device that controls the rotation and inclination of the rotary disc 102, and is specifically a micro processing unit (MPU) or the like.

The bed control device 109 is a device that controls up and down, front and rear, and right and left movements of the bed device 105, and is specifically an MPU or the like. The X-ray control device 110 is a device that controls power input to the X-ray tube device 101, and is specifically an MPU or the like.

The operation unit 120 comprises an input device 121, an image processing device 122, a display device 125, a storage device 123, and a system control device 124. The input device 121 is a device for inputting a name of the subject 10, examination date and time, imaging conditions, or the like, and specifically, is a keyboard, a pointing device, a touch panel, or the like. The image processing device 122 is a device that performs calculation processing on measurement data transmitted from the data collection device 107 to reconstruct a CT image or performs various types of image processing on the CT image. The display device 125 is a device that displays the CT image or the like generated by the image processing device 122, and is specifically a liquid crystal display, a touch panel, or the like. The storage device 123 is a device that stores the data collected by the data collection device 107, the CT image generated by the image processing device 122, or the like, and is specifically a hard disk drive (HDD) or the like. The system control device 124 is a device that controls each unit, and is specifically an MPU or the like.

The X-ray control device 110 controls the power input to the X-ray tube device 101 based on the imaging condition, particularly, an X-ray tube voltage, an X-ray tube current, or the like input from the input device 121, so that the X-ray tube device 101 irradiates the subject 10 with X-rays in accordance with the imaging condition. The X-ray detector 106 detects the X-rays emitted from the X-ray tube device 101 and transmitted through the subject 10 using the detection elements two-dimensionally arranged, and measures the distribution of the transmitted X-rays. The rotary disc 102 is controlled by the gantry control device 108 and rotates based on the imaging condition, particularly, a rotation speed or the like input from the input device 121. The bed device 105 is controlled by the bed control device 109 and is operated based on the imaging condition, particularly, a helical pitch or the like input from the input device 121.

The irradiation with the X-rays from the X-ray tube device 101 and X-ray measurement by the X-ray detector 106 are repeated together with the rotation of the rotary disc 102, and thus projection data at various angles is acquired, and the acquired projection data is transmitted to the image processing device 122. The image processing device 122 reconstructs a CT image by performing inverse projection processing on the transmitted projection data at various angles. The reconstructed CT image is displayed on the display device 125.

Figure 2:
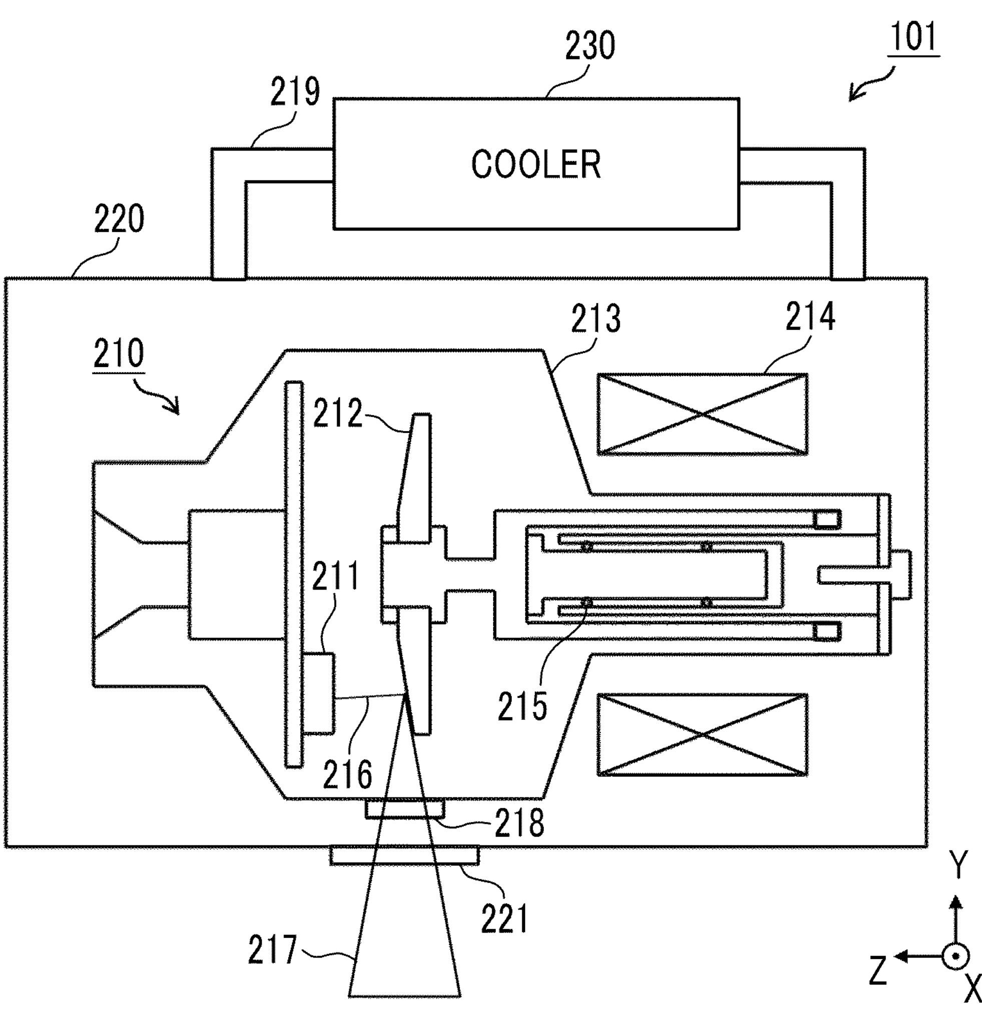
FIG. 2 is a diagram showing an example of an overall configuration of an X-ray tube device.

An example of an overall configuration of the X-ray tube device 101 will be described with reference to FIG. 2. The X-ray tube device 101 comprises an X-ray tube 210, a stator coil 214, a tube container 220, and a cooler 230.

The X-ray tube 210 includes a cathode 211, an anode 212, an envelope 213, and an X-ray window 218.

The cathode 211 generates an electron beam 216 and comprises, for example, a filament or a cold cathode and a focusing electrode. The filament is formed by winding a high-melting point material such as tungsten in a coil shape, and releases electrons by being heated as a current flows therethrough. The cold cathode is formed by sharpening a metal material such as nickel or molybdenum, and releases electrons by field emission by concentrating an electric field on a surface of the cathode. A focusing electrode forms a focusing electric field for focusing the released electrons toward an X-ray focus on the anode 212. The filament or the cold cathode, and the focusing electrode have the same potential.

The anode 212 is an electrode to which a positive potential is applied relative to the cathode 211, and has, for example, a disc shape and comprises a target and an anode substrate. The target is made of a material having a high melting point and a large atomic number, for example, tungsten. The anode substrate is made of a material having a high thermal conductivity, such as copper, and holds the target. The target and the anode substrate have the same potential. The electron beam 216 released from the cathode 211 and accelerated by a potential difference between the cathode 211 and the anode 212 collides with the X-ray focus on the target, and thus X-rays are emitted from the X-ray focus.

The envelope 213 holds the cathode 211 and the anode 212 in a vacuum in order to electrically insulate the cathode 211 and the anode 212 from each other. A potential of the envelope 213 is a ground potential.

The X-ray window 218 is an X-ray window through which X-rays 217 emitted from the X-ray focus is transmitted, and is made of a material having a small atomic number, such as beryllium. Since the electrons released from the anode 212 collide with the X-ray window 218, the X-ray window 218 and a periphery thereof are likely to be heated.

The stator coil 214 generates a magnetic field that is a driving force for rotating the anode 212. A ratio of energy converted into X-rays to energy of the electron beam 216 colliding with the anode 212 is only about 1%, and most of the remaining energy is converted into heat. Therefore, overheating and melting of the anode 212 is prevented by rotating the anode 212 by the magnetic field generated by the stator coil 214. That is, by constantly moving the X-ray focus, which is a portion where the electron beam 216 collides, by rotation of the anode 212, a temperature of the X-ray focus is maintained to be lower than the melting point of the target. The anode 212 is rotatably supported by a rotary bearing 215.

The tube container 220 accommodates the X-ray tube 210 and the stator coil 214 together with insulating oil that electrically insulates the X-ray tube 210. The insulating oil also functions as a cooling medium and circulates in the tube container 220 and the cooler 230 through a pipe 219 linking the tube container 220 and the cooler 230. A radiation window 221 that emits the X-rays 217 is provided in the tube container 220. The radiation window 221 is made of, for example, a material having a small atomic number, such as beryllium, in the same manner as the X-ray window 218.

The cooler 230 is a device that cools the insulating oil. The cooler 230 is linked to the tube container 220 by the pipe 219.

In the X-ray tube device 101, the X-ray focus on which the electron beam 216 collides is a maximum heat source, and it is important to cool the X-ray window 218 provided near the X-ray focus. In addition, since the stator coil 214 that generates the driving force for rotating the anode 212 is also a heat source, it is also important to cool the stator coil 214. While the X-ray window 218 having a relatively small heat capacity is sufficient with cooling in a case where the electron beam 216 collides with the X-ray focus on the anode 212, that is, during X-ray emission, it is preferable to cool the stator coil 214 having a relatively large heat capacity for as long a time as possible.

Therefore, in the X-ray tube device according to the embodiment of the present invention, control is performed such that the insulating oil cooled by the cooler 230 flows into the vicinity of the X-ray window 218 during X-ray emission and flows into the vicinity of the stator coil 214 during X-ray non-emission. With such control, cooling efficiency of the stator coil 214 together with cooling efficiency of the X-ray window 218 can be improved. Since a periphery of the stator coil 214 is a path through which a calorie generated in the X-ray focus on the anode 212 flows, the anode 212 can be smoothly cooled by cooling the stator coil 214.

Figure 3:
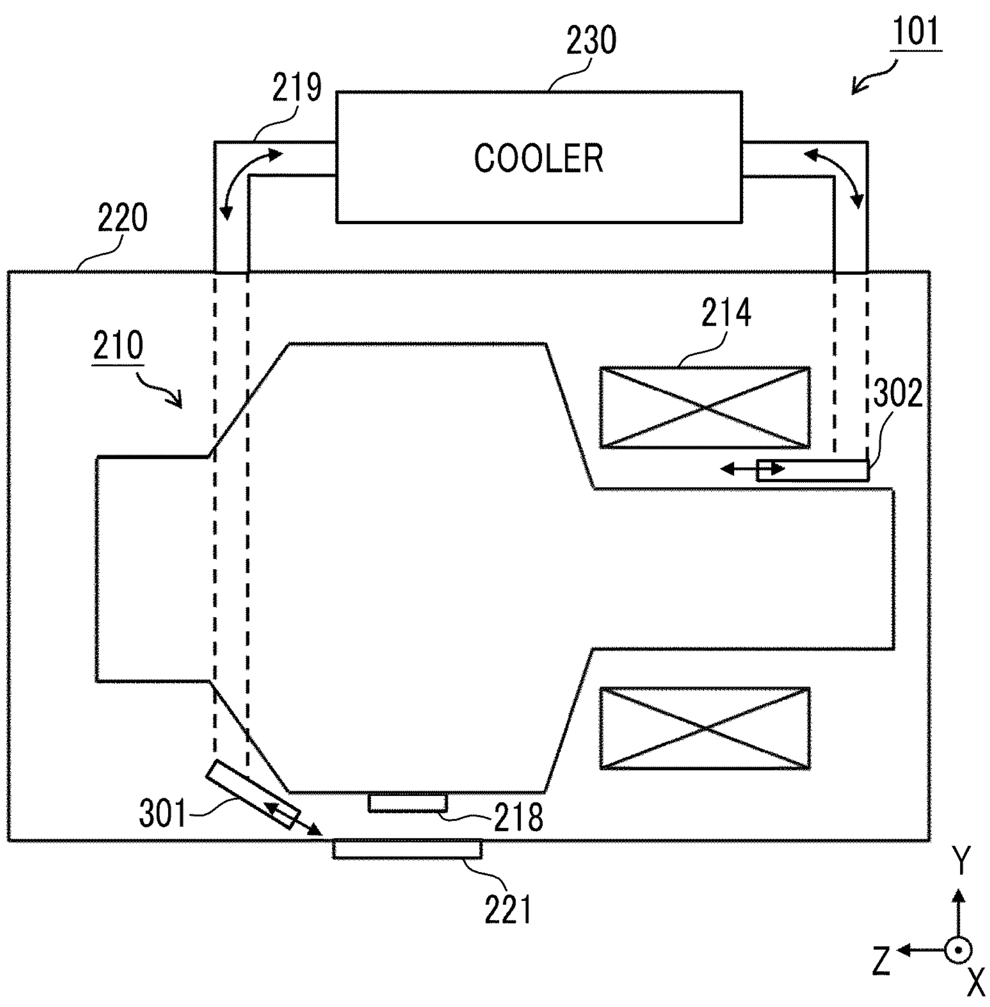
FIG. 3 is a diagram showing an example of outflow/inflow ports for insulating oil.

An example of outflow/inflow ports for the insulating oil will be described with reference to FIG. 3. A first outflow/inflow port 301 is disposed near the X-ray window 218 and is connected to the pipe 219. A second outflow/inflow port 302 is disposed near the stator coil 214 and is connected to the pipe 219. In a case where the X-rays are emitted, the insulating oil cooled by the cooler 230 flows into the tube container 220 through the first outflow/inflow port 301 and flows out from the tube container 220 through the second outflow/inflow port 302. In addition, in a case where the X-rays are not emitted, the insulating oil cooled by the cooler 230 flows into the tube container 220 through the second outflow/inflow port 302 and flows out from the tube container 220 through the first outflow/inflow port 301. That is, since the first outflow/inflow port 301 and the second outflow/inflow port 302 are used as both the inflow port and the outflow port for the insulating oil, the number of components can be reduced. In addition, the flow of insulating oil is reversed between a case where the X-rays are emitted and a case where the X-rays are not emitted.

Figure 4:
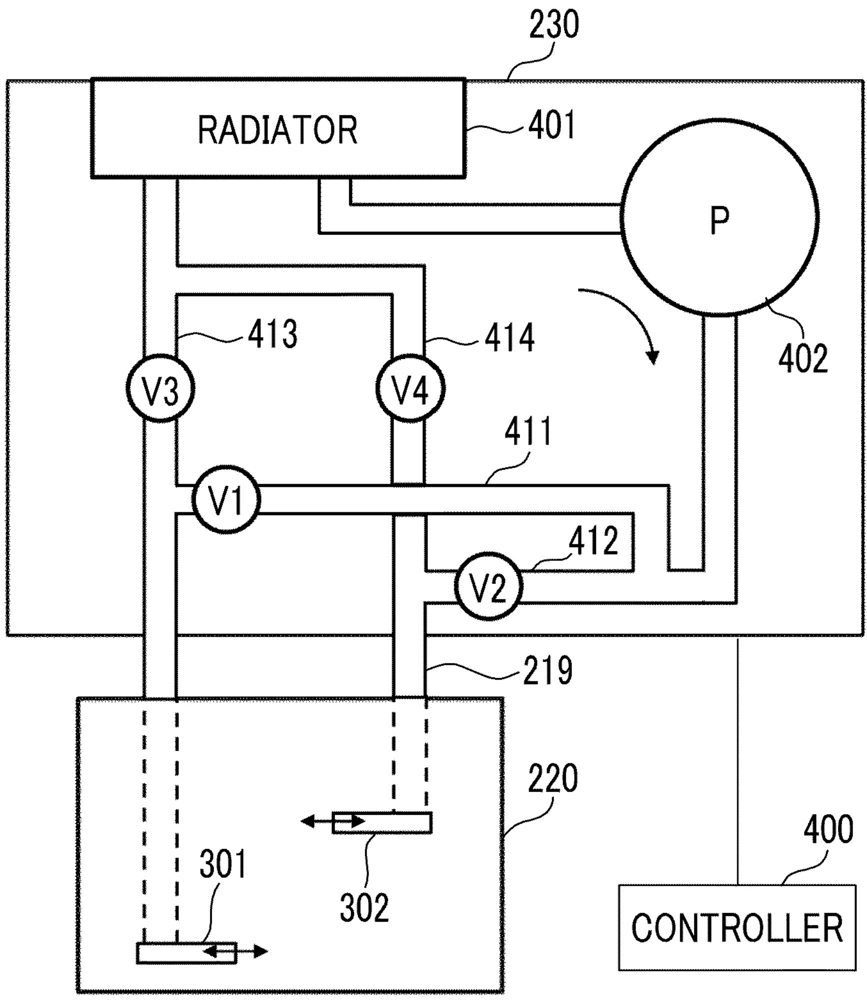
FIG. 4 is a diagram showing an example of a cooler that reverses a flow of the insulating oil.

An example of the cooler 230 that reverses the flow of insulating oil will be described with reference to FIG. 4. The cooler 230 in FIG. 4 includes a radiator 401, a pump 402, four flow channels 411 to 414, and four valves V1 to V4. The radiator 401 is a device that radiates heat of the insulating oil, and is composed of, for example, a plurality of fins provided in a pipe and a fan that sends air to the fins. The pump 402 is a device that feeds the heat-radiated insulating oil to the tube container 220, and feeds the insulating oil in a direction indicated by, for example, an arc arrow.

The first flow channel 411 links the pipe 219 connected to the first outflow/inflow port 301 and the pump 402, and the second flow channel 412 links the pipe 219 connected to the second outflow/inflow port 302 and the pump 402. That is, the flow channel from the pump 402 branches into the first flow channel 411 and the second flow channel 412. The third flow channel 413 links the pipe 219 connected to the first outflow/inflow port 301 and the radiator 401, and the fourth flow channel 414 links the pipe 219 connected to the second outflow/inflow port 302 and the radiator 401. That is, the flow channel from the radiator 401 branches into a third flow channel 413 and a fourth flow channel 414. In addition, the flow channel from the first outflow/inflow port 301 is branched into the first flow channel 411 and the third flow channel 413, and the flow channel from the second outflow/inflow port 302 is branched into the second flow channel 412 and the fourth flow channel 414.

Each of the first valve V1 to the fourth valve V4 is provided in each flow channel of the flow channels, that is, first flow channel 411 to the fourth flow channel 414 and is opened and closed by a controller 400. The controller 400 is composed of an MPU or the like.

Figure 5:
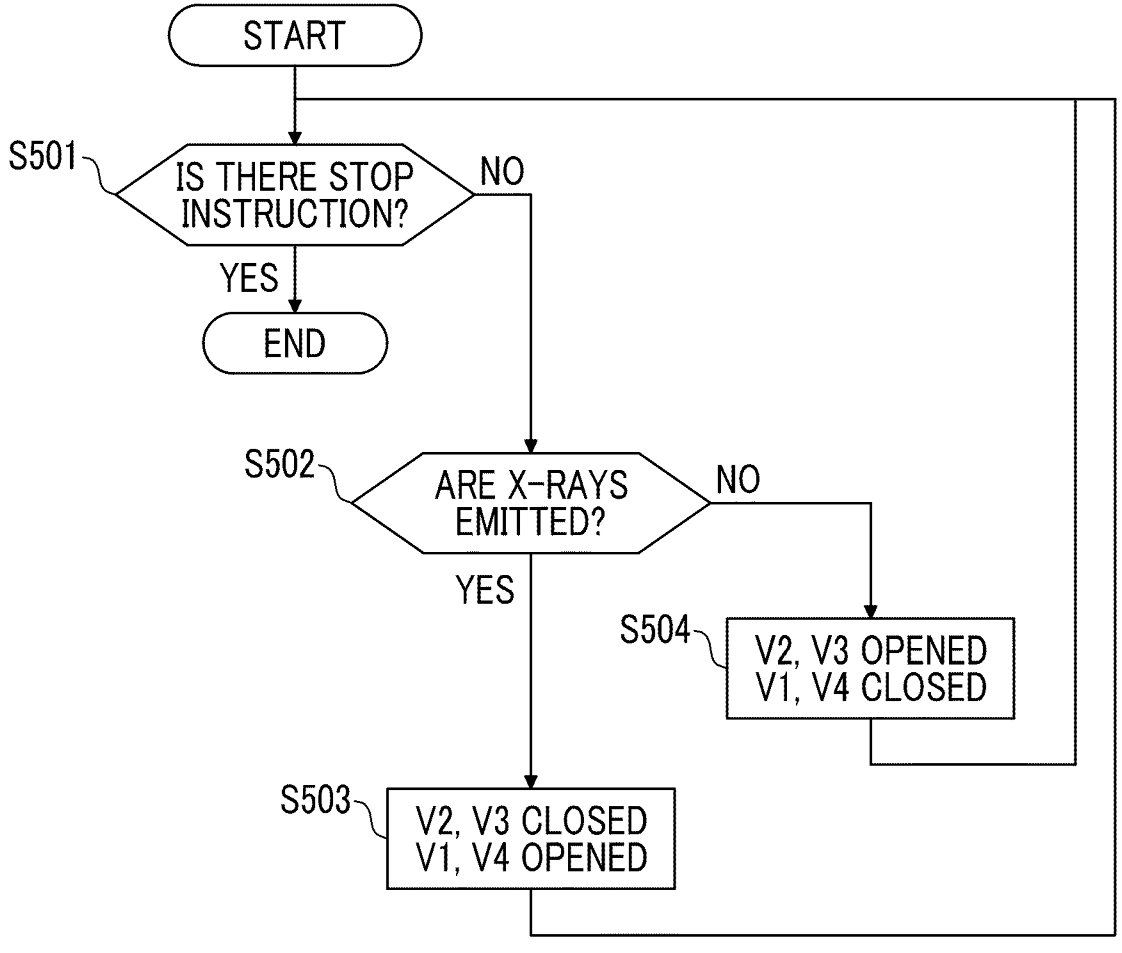
FIG. 5 is a diagram showing an example of a flow of processing of reversing the flow of the insulating oil.

An example of a flow of processing of reversing the flow of the insulating oil by the cooler 230 in FIG. 4 will be described step by step with reference to FIG. 5.

S501

The controller 400 determines whether or not there is a stop instruction. The flow of the processing is ended in a case where there is the stop instruction, and the processing proceeds to S502 in a case where there is no stop instruction. For example, the system control device 124 of the X-ray CT apparatus 1 transmits the stop instruction to the controller 400.

S502

The controller 400 determines whether or not X-rays are emitted. The processing proceeds to S503 in a case where the X-rays are emitted, and the processing proceeds to S504 in a case where the X-rays are not emitted. For example, the system control device 124 or the X-ray control device 110 of the X-ray CT apparatus 1 transmits a signal indicating whether or not X-rays are emitted to the controller 400.

S503

The controller 400 closes the second valve V2 and the third valve V3, and opens the first valve V1 and the fourth valve V4. By opening and closing each valve in this way, the insulating oil that is cooled by the radiator 401 and is fed from the pump 402 flows into the tube container 220 from the first outflow/inflow port 301 through the first flow channel 411. Then, the insulating oil that cools the X-ray window 218 and is circulated in the tube container 220 flows out of the tube container 220 from the second outflow/inflow port 302 and returns to the radiator 401 through the fourth flow channel 414.

S504

The controller 400 closes the first valve V1 and the fourth valve V4, and opens the second valve V2 and the third valve V3. By opening and closing each valve in this way, the insulating oil that is cooled by the radiator 401 and is fed from the pump 402 flows into the tube container 220 from the second outflow/inflow port 302 through the second flow channel 412. Then, the insulating oil that cools the stator coil 214 and is circulated in the tube container 220 flows out of the tube container 220 from the first outflow/inflow port 301 and returns to the radiator 401 through the third flow channel 413.

By the flow of the processing described with reference to FIG. 5, the insulating oil cooled by the cooler 230 flows into the tube container 220 from the first outflow/inflow port 301 to cool the X-ray window 218 during emission of X-rays, and flows from the second outflow/inflow port 302 to cool the stator coil 214 during non-emission. That is, the cooling efficiency of the stator coil 214 together with the cooling efficiency of the X-ray window 218 can be improved. In addition, although the flow of the insulating oil in the tube container 220 is reversed, a pressure on the pump 402 does not change, so that a failure is unlikely to occur.

It should be noted that the determination in S502 is not limited to whether or not the X-ray is emitted. In the X-ray CT apparatus 1, since the X-rays are emitted after the rotary disc 102 starts to rotate and reaches a constant rotation speed, it may be determined in S502 whether or not the rotary disc 102 is rotating. By determining in S502 that whether or not the rotary disc 102 is rotating, even in a case where a time lag occurs in a signal transmitted to the controller 400, the X-ray window 218 is always cooled in a case where the X-rays are emitted.

Another example of the cooler 230 that reverses the flow of the insulating oil will be described with reference to FIG. 6. The cooler 230 in FIG. 6 includes the radiator 401, a gear pump 601, a bypass 602, and a bypass valve VB. The radiator 401 is the same as that in FIG. 4, and the bypass 602 and the bypass valve VB may not be provided.

Figure 6:
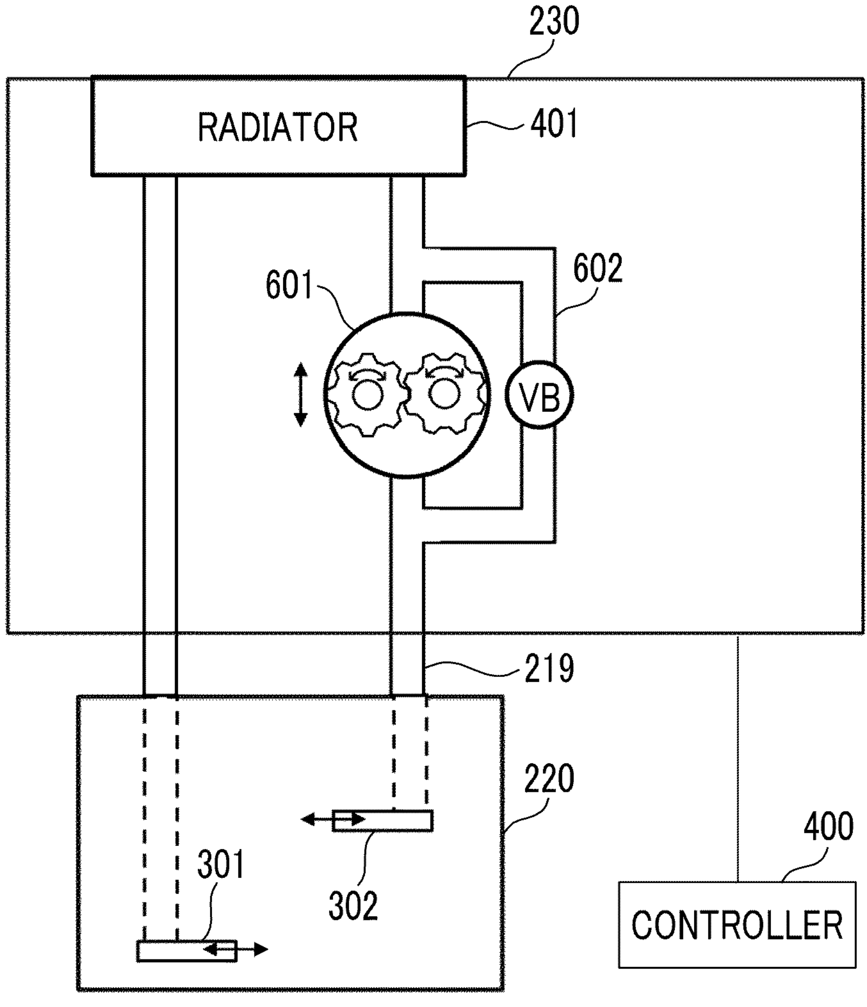
FIG. 6 is a diagram showing another example of a cooler that reverses the flow of the insulating oil.

The gear pump 601 is a device that feeds the insulating oil, and is capable of switching a feeding direction of the insulating oil to an upward direction or a downward direction in FIG. 6 depending on a direction in which two meshing gears rotate. That is, the controller 400 can reverse the flow of the insulating oil by switching the rotation direction of the gears of the gear pump 601 in accordance with whether or not the X-rays are emitted.

The bypass 602 is a flow channel avoiding the gear pump 601. The bypass valve VB is provided in the bypass 602 and is opened and closed by the controller 400. In a case where the flow of the insulating oil is reversed by the gear pump 601, the gear pump 601 or the flow channel may be damaged because of an impact generated in the flow channel. Therefore, the controller 400 opens the bypass valve VB in a case of reversing the flow of the insulating oil, so that the impact during the reversal is released through the bypass 602, and the damage to the gear pump 601 or the flow channel can be prevented. The controller 400 closes the bypass valve VB in a case where a predetermined time or longer has elapsed after the flow of the insulating oil is reversed. The predetermined time is set to a time required for the flow in the flow channel to be stabilized after the flow of the insulating oil is reversed.

With the cooler 230 shown in FIG. 6, it is possible to cause the insulating oil to flow into the tube container 220 from the first outflow/inflow port 301 to cool the X-ray window 218 during emission of X-rays, and to cause the insulating oil to flow from the second outflow/inflow port 302 to cool the stator coil 214 during non-emission. That is, the cooling efficiency of the stator coil 214 together with the cooling efficiency of the X-ray window 218 can be improved. In addition, the cooler 230 in FIG. 6 can have a simple structure as compared with that in FIG. 4. In order to improve the cooling efficiency of the X-ray window 218 and the stator coil 214, the flow of the insulating oil may not be reversed.

Figure 7:
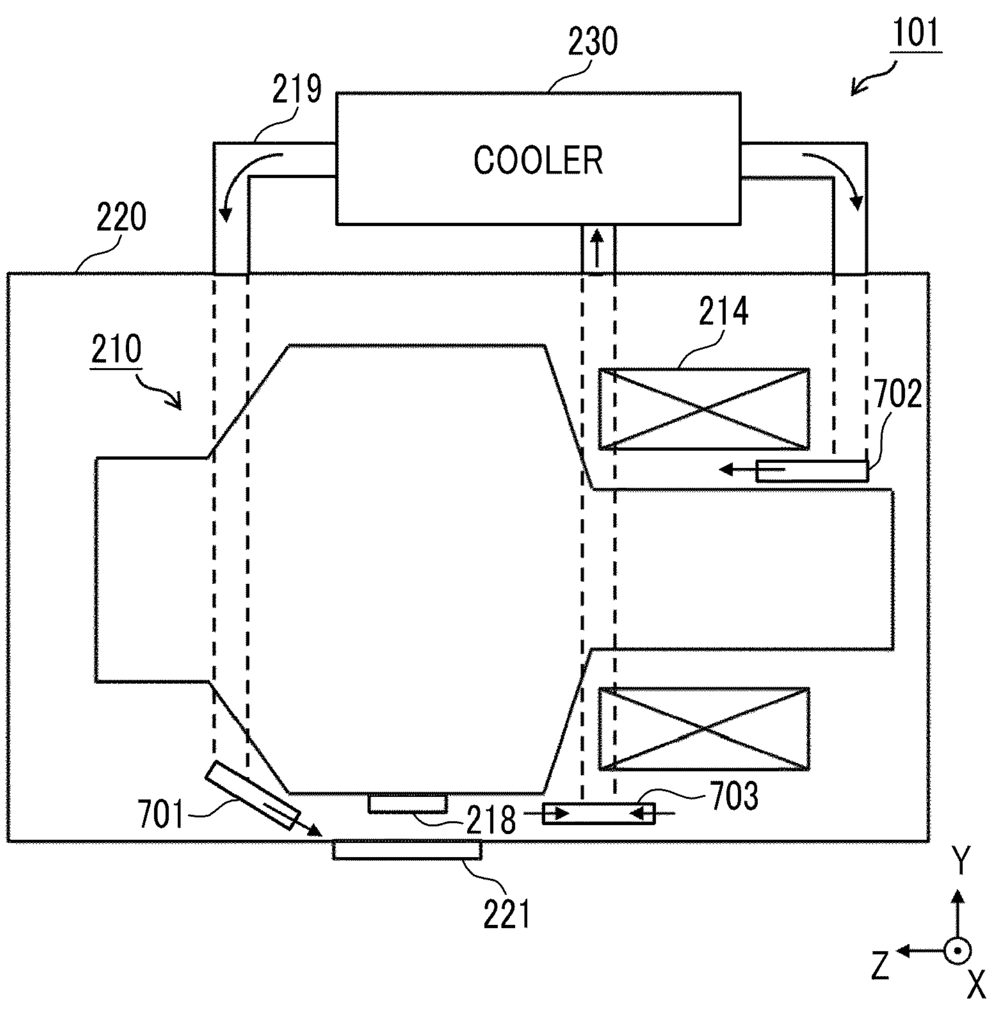
FIG. 7 is a diagram showing an example of an inflow port and an outflow port for the insulating oil.

An example of an inflow port and an outflow port in a case where the flow of insulating oil is not reversed will be described with reference to FIG. 7. A first inflow port 701 is disposed near the X-ray window 218 and is connected to the pipe 219 through which the insulating oil is fed from the cooler 230. The second outflow/inflow port 302 is disposed near the stator coil 214 and is connected to the pipe 219 through which the insulating oil is fed from the cooler 230. An outflow port 703 is disposed in the tube container 220 and is connected to the pipe 219 through which the insulating oil is returned to the cooler 230.

In a case where the X-rays are emitted, the insulating oil cooled by the cooler 230 flows into the tube container 220 through the first inflow port 701 and returns from the tube container 220 to the cooler 230 through the outflow port 703. In addition, in a case where the X-rays are not emitted, the insulating oil cooled by the cooler 230 flows into the tube container 220 through a second inflow port 702 and returns from the tube container 220 to the cooler 230 through the outflow port 703. That is, the inflow port of the insulating oil is switched between the case where the X-rays are emitted and the case where the X-rays are not emitted.

An example of the cooler 230 that switches the inflow port of the insulating oil will be described with reference to FIG. 8. The cooler 230 in FIG. 8 includes the radiator 401, the pump 402, the first flow channel 411, the second flow channel 412, a fifth flow channel 800, the first valve V1, and the second valve V2. The radiator 401 and the pump 402 are the same as those in FIG. 4.

The first flow channel 411 links the pipe 219 connected to the first inflow port 701 and the pump 402, and includes the first valve V1. The second flow channel 412 links the pipe 219 connected to the second inflow port 702 and the pump 402, and includes the second valve V2. The flow channel from the pump 402 is branched into the first flow channel 411 and the second flow channel 412. The fifth flow channel 800 links the pipe 219 connected to the outflow port 703 and the radiator 401.

The opening and closing of the first valve V1 and the second valve V2 are controlled by the controller 400. Specifically, the first valve V1 is opened and the second valve V2 is closed during emission of X-rays, and the first valve V1 is closed and the second valve V2 is opened during non-emission of X-rays. With such control, the insulating oil cooled by the cooler 230 flows inside from the first inflow port 701 to cool the X-ray window 218 during emission of X-rays, and flows inside from the second inflow port 702 to cool the stator coil 214 during non-emission. That is, the cooling efficiency of the X-ray window 218 and the stator coil 214 can be improved.

Figure 8:
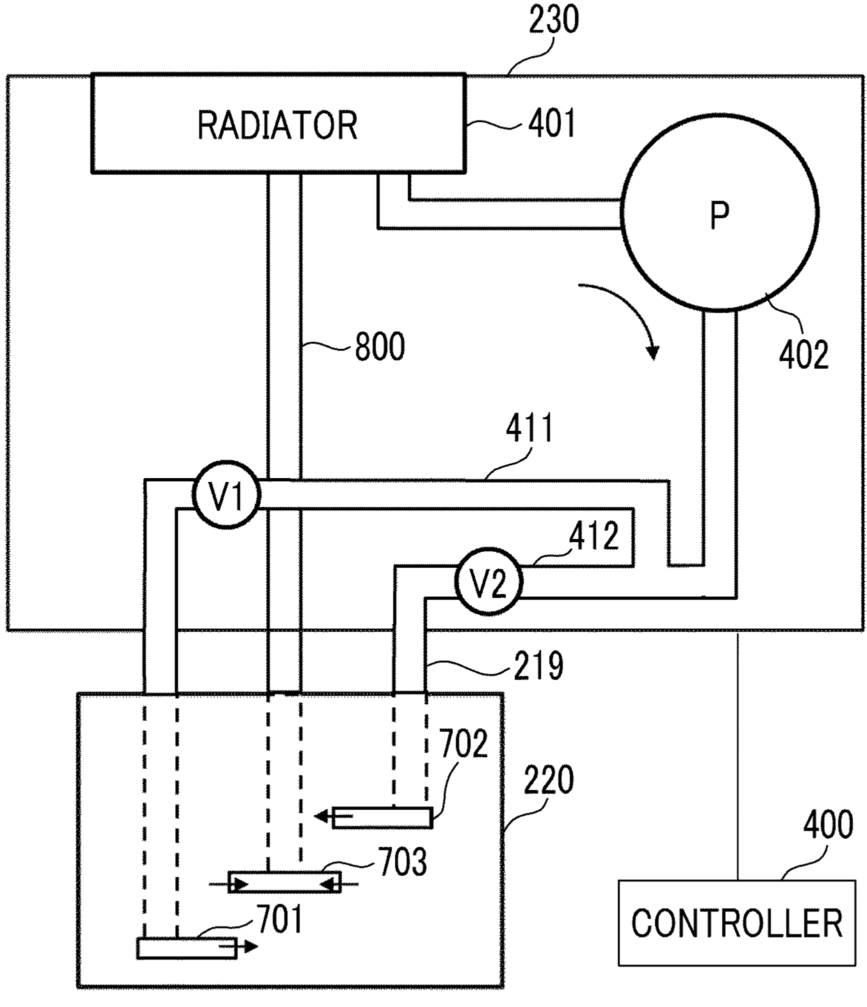
FIG. 8 is a diagram showing an example of a cooler that switches inflow of the insulating oil.

In the cooler in FIG. 8, the first valve V1 and the second valve V2 may not be closed. For example, the first valve V1 may be opened and the second valve V2 may be slightly opened during emission of X-rays, and the second valve V2 may be opened and the first valve V1 may be slightly opened during non-emission of X-rays. By opening the first valve V1 and the second valve V2 by a slight opening rate of, for example, about 5%, both the X-ray window 218 and the stator coil 214 can be constantly cooled. In addition, the opening rates of the first valve V1 and the second valve V2 may be controlled based on temperatures of the X-ray window 218 and the stator coil 214.

The embodiment of the present invention has been described above. It should be noted that the present invention is not limited to the above-described embodiment, and the components can be modified and embodied without departing from the gist of the invention. In addition, a plurality of components disclosed in the above-described embodiment may be combined as appropriate. Further, some components may be deleted from all the components described in the above-described embodiment.

EXPLANATION OF REFERENCES

1: X-ray CT apparatus
10: subject
100: scan gantry unit
101: X-ray tube device

102: rotary disc
103: collimator
104: opening portion
105: bed device
106: X-ray detector
107: data collection device
108: gantry control device
109: bed control device
110: X-ray control device
120: operation unit
121: input device
122: image processing device
123: storage device
124: system control device
125: display device
210: X-ray tube
211: cathode
212: anode
213: envelope
214: stator coil
215: rotary bearing
216: electron beam
217: X-ray
218: X-ray window
219: pipe
220: tube container
221: radiation window
230: cooler
301: first outflow/inflow port
302: second outflow/inflow port
400: controller
401: radiator
402: pump
411: first flow channel
412: second flow channel
413: third flow channel
414: fourth flow channel
601: gear pump
602: bypass
701: first inflow port
702: second inflow port
703: outflow port
800: fifth flow channel
V1: first valve
V2: second valve
V3: third valve
V4: fourth valve
VB: bypass valve

What is claimed is:

1. An X-ray tube device comprising:
an X-ray tube including an envelope that holds, in a vacuum, a cathode generating an electron beam and an anode emitting an X-ray by collision of the electron beam, and an X-ray window through which the X-ray is transmitted;
a stator coil configured to generate a driving force for rotating the anode;
a tube container configured to accommodate the X-ray tube and the stator coil together with insulating oil; and
a cooler configured to cool the insulating oil,
wherein the X-ray tube device includes
a first inflow port connected to a pipe linking the tube container and the cooler and disposed near the X-ray window,
a second inflow port connected to the pipe and disposed near the stator coil, and
a controller configured to:
cause the insulating oil to flow into the tube container through the first inflow port in a case where the X-ray is emitted,
cause the insulating oil to flow out from the tube container through the second inflow port in a case where the X-ray is emitted,
cause the insulating oil to flow into the tube container through the second inflow port in a case where the X-ray is not emitted, and
cause the insulating oil to flow out from the tube container through the first inflow port in a case where the X-ray is not emitted.

2. The X-ray tube device according to claim 1,
wherein the cooler includes a radiator that radiates heat of the insulating oil, a pump that feeds the insulating oil, a first flow channel that links the pipe connected to the first inflow port and the pump, a second flow channel that links the pipe connected to the second inflow port and the pump, a third flow channel that links the pipe connected to the first inflow port and the radiator, a fourth flow channel that links the pipe connected to the second inflow port and the radiator, a first valve provided in the first flow channel, a second valve provided in the second flow channel, a third valve provided in the third flow channel, and the fourth valve provided in the fourth flow channel, and
the controller closes the second valve and the third valve and opens the first valve and the fourth valve in a case where the X-ray is emitted, and closes the first valve and the fourth valve and opens the second valve and the third valve in a case where the X-ray is not emitted.

3. The X-ray tube device according to claim 1,
wherein the cooler includes a radiator that radiates heat of the insulating oil, and a gear pump that feeds the insulating oil, and
the controller reverses the gear pump between a case where the X-ray is emitted and a case where the X-ray is not emitted.

4. The X-ray tube device according to claim 3,
wherein the cooler further includes a bypass that avoids the gear pump, and a bypass valve that is provided in the bypass, and
the controller opens the bypass valve in a case where the gear pump is reversed.

5. The X-ray tube device according to claim 1,
wherein the controller causes the insulating oil to flow into the tube container also from the second inflow port in a case where the X-ray is emitted, and causes the insulating oil to flow into the tube container also from the first inflow port in a case where the X-ray is not emitted.

6. An X-ray CT apparatus that generates a tomographic image of a subject, the X-ray CT apparatus comprising:
the X-ray tube device according to claim 1.

7. The X-ray CT apparatus according to claim 6,
wherein a stop instruction or whether or not the X-ray is emitted is transmitted to the controller.

* * * * *